United States Patent [19]

Iglesia et al.

[11] Patent Number: 4,754,092

[45] Date of Patent: Jun. 28, 1988

[54] REDUCING METHANE PRODUCTION AND INCREASING LIQUID YIELDS IN FISCHER-TROPSCH REACTIONS

[75] Inventors: Enrique Iglesia, Clinton; Rostam Madon, Flemington, both of N.J.

[73] Assignee: Exxon Research and Engineering Company, Florham Park, N.J.

[21] Appl. No.: 944,656

[22] Filed: Dec. 22, 1986

Related U.S. Application Data

[62] Division of Ser. No. 814,680, Dec. 30, 1985, abandoned.

[51] Int. Cl.$^4$ ............................................. C07C 1/04
[52] U.S. Cl. ................................. 585/469; 518/705; 518/715; 518/719; 518/721; 585/315; 585/638; 585/733
[58] Field of Search ............... 585/315, 469, 638, 733; 518/705, 708, 715, 719, 721

[56] References Cited

U.S. PATENT DOCUMENTS

| | | | |
|---|---|---|---|
| 4,206,135 | 6/1980 | Kugler et al. | 518/717 |
| 4,544,674 | 10/1985 | Fiato et al. | 518/717 |
| 4,547,525 | 10/1985 | Kim | 518/713 |
| 4,622,308 | 11/1986 | Koikeda et al. | 502/66 |

FOREIGN PATENT DOCUMENTS 140680 12/1947 Australia ............................ 518/717

*Primary Examiner*—Asok Pal
*Attorney, Agent, or Firm*—Richard E. Nanfeldt

[57] ABSTRACT

A process for reducing methane formation and increasing liquid ($C_5+$) yields in Fischer-Tropsch hydrocarbon synthesis processes of CO and $H_2$ comprising adding one or more olefins to the reactor bed at a point below 10% of the distance from the top to the bottom of the reactor bed and above a point 10% above the bottom of the reactor bed to the top of the reactor bed in an amount sufficient to reduce said methane formation.

8 Claims, No Drawings

REDUCING METHANE PRODUCTION AND INCREASING LIQUID YIELDS IN FISCHER-TROPSCH REACTIONS

This is a Divisional application of the U.S. application Ser. No. 814,680, filed Dec. 30, 1985, now abandoned.

BACKGROUND OF THE INVENTION

1. Field of the Invention

This invention relates to reducing methane production and increasing liquid ($C_5+$) yields in Fischer-Tropsch hydrocarbon synthesis reactions by recycling olefins separated from the product directly into the reactor bed. More particularly, this invention relates to reducing methane production in catalytic Fischer-Tropsch reactions wherein hydrocarbons are synthesized from a feed comprising a mixture of CO and $H_2$ and adding one or more olefins directly to the reactor bed, wherein the olefin is separated from the product stream or obtained from an independent source and then added directly to the reactor bed.

2. Background of the Invention

The production of hydrocarbons from mixtures of $H_2$ and CO via the Fischer-Tropsch process is well known to those skilled in the art. As opposed to the well known "methanation" process, which produces methane as synthetic natural gas from mixtures of $H_2$ and CO, the Fischer-Tropsch process is more generally aimed at producing higher value products, such as chemical feedstocks and liquid fuels. Thus, high methane make is undesirable in Fischer-Tropsch synthesis processes because it is a relatively low value product which is formed at the expense of more desirable products. It is also uneconomical to try to convert the so-formed methane back into a CO and $H_2$ mixture and recycle it back into the reactor.

Methane make in Fischer-Tropsch reactions is often expressed by a term known as methane selectivity and also carbon selectivity (% of CO converted which appears as methane) which is almost identical to weight percent. Methane selectivity can be defined by either of two methods, which are: (a) mole percent $CH_4$ produced based on the amount of CO consumed; or (b) weight percent of $CH_4$ produced based on total hydrocarbon products formed.

Many different catalysts and processes have been disclosed for Fischer-Tropsch synthesis, some of which have extremely high methane make. Thus, U.S. Pat. No. 4,077,995 discloses synthesis of $C_1$–$C_4$ aliphatic hydrocarbons over a catalyst comprising a sulfided mixture of CoO, $Al_2O_3$ and ZnO, while U.S. Pat. No. 4,039,302 discloses $C_1$–$C_3$ hydrocarbon production using a mixture of the oxides of Co, Al, Zn and Mo. U.S. Pat. No. 4,151,190 discloses $C_2$–$C_4$ hydrocarbons from mixtures of CO and $H_2$ using a supported catalyst comprising a metal oxide or sulfide of Mo, W, Re, Ru, Ni or Pt, plus an alkali or alkaline earth metal, with Mo-K on carbon being preferred. U.S. Pat. Nos. 4,243,553 and 4,243,554 disclose $MoS_2$ as a Fischer-Tropsch catalyst. Many other catalysts are known to be useful for Fischer-Tropsch synthesis employing metals such as iron, copper, titania, etc. These are known to those skilled in the art.

The type of catalyst used and process conditions employed have an important bearing on $CH_4$ selectivity. For example, nickel gives a high $CH_4$ selectivity and is used mainly as a methanation catalyst. Methane selectivity usually increases with increasing temperature, decreasing pressure and increasing the $H_2$/CO ratio of the feed. Accordingly, process conditions are selected so as to minimize $CH_4$ selectivity and $C_2$–$C_4$ selectivity, also while maintaining a relatively high reaction rate, as is well known to those skilled in the art.

It is known that $CH_4$ selectivity is influenced by the choice of promoter and support, such as alkali metal promoters reducing $CH_4$ selectivities of iron catalysts. It is also known in the art that noble metals, such as ruthenium, supported on inorganic refractory oxide supports exhibit superior hydrocarbon synthesis characteristics with relatively low methane production. Thus, U.S. Pat. No. 4,088,671 suggests minimizing methane production by using a small amount of Ru on a cobalt catalyst. Examples of supported ruthenium catalysts suitable for hydrocarbon synthesis via Fischer-Tropsch reactions are disclosed in U.S. Pat. Nos. 4,042,614 and 4,171,320, the disclosures of which are incorporated herein by reference. It is also known that the type of support used also influences methane production. In the case of supported ruthenium catalysts the use of a titania or titania-containing support will result in lower methane production than, for example, a silica, alumina or manganese oxide support.

The present invention differs from U.S. Ser. No. 563,109, filed on Dec. 19, 1983, in that in U.S. Ser. No. 563,109 alpha olefin was added directly to the feed of the CO/$H_2$, whereas in the instant invention the alpha olefin, which is recycled from the product stream or obtained from a separate, independent source, is added directly into the reactor bed through an inlet port in the side of the tubular reactor, wherein the inlet port is positioned below a point which is 10% of the distance from the top of the reactor bed to the bottom of the reactor bed and above a point which is 10% of the distance from the bottom of the reactor bed to the top of the reactor bed.

Those skilled in the art recognize the need for reducing methane production still further, even when employing catalysts comprising ruthenium supported on titania.

SUMMARY OF THE INVENTION

It has now been discovered that liquid ($C_5+$) yields and methane production in Fischer-Tropsch hydrocarbon synthesis reactions is reduced by adding one or more olefins directly into the reactor bed. Thus, the instant invention relates to a process for reducing methane production in Fischer-Tropsch processes wherein hydrocarbons are synthesized from feeds comprising mixtures of CO and $H_2$ and by adding at least one olefin to the reactor bed, wherein the olefin is obtained by separation from the product stream and recycled to the reactor bed or from an independent source, such as processing the paraffinic product of the Fischer-Tropsch reaction through a dehydrogenation reactor to convert the paraffins into olefins. In a preferred embodiment, the olefin or olefins will comprise one or more $C_2$–$C_{20}$ alpha olefins, wherein the olefin to CO mole ratio in the reactor is from about 1/20 to 5/1, more preferably from about 1/10 to about 2/1, and most preferably from about 1/5 to about 1/1. The catalyst will comprise at least one Group VIII metal supported on an inorganic refractory oxide support. Additionally, cobalt or iron catalyst can be readily employed. In a particularly preferred embodiment the catalyst will comprise ruthenium supported on titania.

DETAILED DESCRIPTION OF THE INVENTION

It has now been discovered that methane production in Fischer-Tropsch hydrocarbon synthesis reactions is reduced by adding one or more olefins directly into the reactor bed. Thus, the instant invention relates to a process for reducing methane production in Fischer-Tropsch processes wherein hydrocarbons are synthesized from feeds comprising mixtures of CO and $H_2$ and by adding at least one olefin to the reactor bed, wherein the olefin is obtained by separation from the product stream and recycled to the reactor bed or from an independent source. In a preferred embodiment, the olefin or olefins will comprise one or more $C_2$–$C_{20}$ alpha olefins, wherein the olefin to CO mole ratio in the reactor is from about 1/20 to 5/1, more preferably from about 1/10 to about 2/1, and most preferably from about 1/5 to about 1/1. The catalyst will comprise at least one Group VIII metal supported on an inorganic refractory oxide support. In a particularly preferred embodiment the catalyst will comprise ruthenium supported on titania. Additionally, cobalt or iron catalyst can be readily employed.

Preferred olefins useful in the process of the instant invention include alpha olefins of the type R—CH=$CH_2$ wherein R is hydrogen or an alkyl group having about 1 to about 17 carbon atoms, more preferably the alkyl group has about 1 to about 11 carbon atoms, and most preferably the alkyl group has about 1 to about 8 carbon atoms. Still more preferable are $C_2$–$C_{10}$ alpha olefins. The amount of alpha olefin recycled to the reactor bed will be sufficient to maintain an olefin to CO mole ratio of from about 1/100 to 5/1, more preferably about 1/20 to 5/1, and most preferably about 1/10 to about 2/1. Also, internal olefins where unsaturation is away from the terminal carbon can also be added beneficially to the CO/$H_2$ feed.

Although the process of the instant invention may be practiced in the presence of any suitable Fischer-Tropsch catalyst, in a preferred embodiment it will be practiced in the presence of a catalyst comprising one of more Group VIII metals supported on an inorganic refractory oxide support, preferably ruthenium or cobalt supported on such a support. Thus, suitable supports include oxides of titania, niobia, vanadium, tantalum, silica, alumina, manganese and mixtures thereof. Preferably the catalyst support will be selected from the group consisting of titania, zirconium titanate, mixtures of titania and alumina, mixtures of titania and silica, alkaline earth titanates, alkali titanates, rare earth titanates and mixtures of any one of the foregoing with supports selected from the group consisting of vanadia, niobia, tantala, alumina, silica and mixtures thereof. Thus, in a particularly preferred embodiment of this invention the process will be carried out in the presence of a catalyst comprising ruthenium supported on a titania support. Alternatively, the catalyst can comprise cobalt or iron supported on one of the aforementioned inorganic refractory oxides.

In general, the amount of cobalt catalytic metal present is about 1 to about 50 weight percent of the total catalyst composition, more preferably from about 10.0 to about 25 weight percent.

Iron catalysts containing about 10 to about 60 weight percent iron, more preferably about 20 to about 60 weight percent, and most preferably about 30 to about 50 weight percent, are unsupported, but promoted with refractory metal oxide ($SiO_2$, $Al_2O_3$, etc.), alkali (K, Na, Rb) and Group IB metal (Cu, Ag). These catalysts are usually calcined, but usually not reduced, rather they are brought up to reaction temperature directly in the CO/$H_2$ feed.

In general, the amount of ruthenium catalytic metal present on the catalyst will generally range from about 0.01 to 50 weight percent of the total catalyst composition, more preferably from about 0.1 to 5.0 weight percent and most preferably from about 0.5 to about 5 weight percent.

In general, in the process of this invention the Fischer-Tropsch reactor temperature will broadly range from about 100° C. to 500° C., more preferably from about 150° C. to 300° C. and most preferably about 200° C. to about 270° C., at a pressure of about 100 to about 10,000 kPa, more preferably about 300 to about 5,000 kPa and most preferably about 500 to about 3,000 kPa. The space velocity ($V_1$) of the feed gas ($H_2$+CO) will range from about 10 to 10,000 standard $cm^3$/hr-($cm^3$ of catalyst), more preferably about 100–4,000 and most preferably about 200 to about 2,000. The space velocity ($V_2$) of the alpha olefin will range from about 0.1 to about 20,000 standard $cm^3$/hr-($cm^3$ of catalyst), more preferably about 3–4,000 and most preferably about 10 to about 1,000. Thus, the volume ratio of $V_1/V_2$ is about 0.005 to about 10,000, more preferably about 0.02 to about 1,000 and most preferably about 0.5 to about 200. The hydrogen to carbon monoxide mole ratio of the feed gas, $H_2$/CO, will range from about 0.5 to 10 and preferably from about 1 to 3.

The alpha olefin is selected into the reactor through an inlet port in the sidewall or center of the reactor, wherein the part is positioned below a point which is 10% of the distance from the top of the reactor bed to the bottom of the reactor bed and above a point which is 10% of the distance from the bottom of the reactor bed to the top of the reactor bed.

The reactor bed can comprise a single reactor bed of one catalyst system or it can comprise two catalyst beds with different Fischer-Tropsch synthesis catalysts separated by an inert inter-stage knock-out zone. The alpha olefin can also be injected through an inlet port located at the inter-stage knock-out zone. Alternatively, the system can comprise a plurality of tubular reactors joined in a serial fluid communication wherein the alpha olefin is injected into the system either within the first reactor bed or subsequent thereto with or without interstage knock-out zone.

DESCRIPTION OF THE PREFERRED EMBODIMENTS

The invention will be more readily understood by reference to the following Examples.

Fischer-Tropsch Hydrocarbon Synthesis

Experimental Procedure

Anywhere from about 5 to 40 g of catalyst was loaded into a stainless steel reactor with an ID of 0.78 cm, having a thermocouple placed within the catalyst bed to measure temperature. The reactor was flushed with He at a flow rate of 500 cc/min. and then pressurized (in He) at 30 atmospheres to confirm the integrity of the unit. The He in the reactor was then brought back to 1 atmosphere and replaced with $H_2$ at a space velocity between 200–600 v/v/hr at room temperature. The temperature was raised in approximately 2 to 3 hours to a final reduction temperature of between 400° C. to 500° C. and held at this temperature overnight.

After reduction, each catalyst was brought on stream in either one of two ways, which were found to be substantially equivalent. In one method, the reduced catalyst was treated for 15 to 50 hours at 1 atmosphere $2H_2/CO$ at 200° C. (the space velocity of the $H_2/CO$ used was varied from 200–1,000 cm$^3H_2$+CO h.(cc catalyst). The conditions in the reactor were then adjusted to the desired temperature, pressure and space velocity. In the other method, the atmospheric treatment in $H_2/CO$ was not done and the catalysts were brought on-stream at the desired experimental pressure in $H_2/CO$, but an initial low temperature of 150°–170° C., which was then slowly raised (in 1 to 5 hours) to the desired experimental temperature.

EXAMPLES

In all of the Examples, the determination of the Fischer-Tropsch synthesis activity towards the various products was measured by employing an on-line gas chromatograph using an isothermal, fixed-bed, stainless steel reactor (0.78 cm ID) into which from about 5 to 40 g of catalyst was loaded. A thermocouple was placed within the catalyst bed to measure the reaction temperature.

Example 1

Preparation of Ru Catalyst

Titanium dioxide supports prepared by pressing Degussa P-25 powder (20–70% rutile) into wafers using a hydraulic press at a pressure of about 20,000 lb/in$^2$. The wafers were then crushed in a mortar to a coarse powder and sieved to retain the 80–140 mesh (U.S. standard) fraction for all the $TiO_2$ supported catalysts. The so-formed titanium dioxide support samples were calcined in flowing air overnight (about 1 liter per minute) at a temperature of 550° C. to 600° C. The calcined samples were then reduced in hydrogen flowing at a rate of 1 liter per minute by heating from room temperature to 450° C. for 4 hours, after which the sample was cooled in flowing $H_2$, flushed with He and discharged. These reduced samples possessed the characteristic blue-gray color of surface-reduced $TiO_2$.

Catalysts were produced by impregnating the support material with a ruthenium nitrate/acetone mixture. The nitrate was obtained from Engelhardt as 10% weight ruthenium metal in nitric acid.

The nitrate-impregnated $TiO_2$ was reduced in flowing hydrogen (1 l/min.) as follows: (a) heated from room temperature to 100° C. and held for 0.5 hours; (b) heated from 100° C. to 450° C. at 3° C./min. and held for 4 hours; (c) cooled in $H_2$ to room temperature overnight; and (d) flushed in the reduction cell with He or Ar (1 l/min.) for one hour. Each sample of reduced catalyst was then passivated by introducing 1% $O_2$ into the He stream and then increasing the $O_2$ content to 100% over a period of from about 2–3 hours.

Example 2

Preparation of Cobalt Catalyst

Degussa P-25 $TiO_2$ was treated with acetone, dried at 90° C. and mulled with 9.6 weight percent Sterotex (vegetable stearine). This material was tableted to ⅜ inch size, using a pilling pressure which yielded a material of 0.35–0.40 ml/g pore volume. The ⅜ inch pills were crushed and screened to 42–80 mesh size and calcined in flowing air at 500° C. for 4 hours to burn out the sterotex. Portions were then re-calcined in flowing air at 650° C. for 16 hours to obtain a high rutile content and screened to 80–150 mesh size. The support composite used to prepare this catalyst was 97% rutile, 13.6 m$^2$/g, 0.173 ml/g.

Impregnation Procedure 108.8 g cobaltous nitrate (Co(NO$_2$)$_2$.6H$_2$O and 16 ml aqueous perrhenic acid solution (52 mg Re/ml) were then dissolved in about 300 ml acetone in a 1 liter round bottom flask. 160 g TiO$_2$ (YAX-0487) was added and the mixture placed on a rotary evaporator until dry. The catalyst was dried in a vacuum oven at 140° C. for 18 hours and calcined in flowing air at 250° C. for 3 hours. The calcined catalyst was re-screened to remove the small amount of fines generated during preparation.

Cobalt Catalyst Preparation

Analytical inspections for the catalyst are given below:

| | |
|---|---|
| Cobalt, Wt. % | 11.3 |
| Rhenium, Wt. % | 0.42 |
| Sodium ppm | 369 |
| % Rutile (ASTM D 3720-78) | 97 |
| Surface Area, m$_2$/g | 14.6 |
| Pore Volume, ml/g | 0.122 |
| Bulk Density, g/ml | 1.41 |

Besides quantifying rutile content, the x-ray diffraction spectrum indicates the presence of Co$_3$O$_4$.

Example 3

Effect of Ethylene Feed-Cobalt Catalysts

The general procedure described for Fischer-Tropsch hydrocarbon synthesis was modified as follows in Examples 3 and 4.

The catalyst was started in H$_2$/CO at a space velocity required to achieve 25–45% CO conversion and at 1,700–2,500 Kpa. An ethylene/argon mixture was mixed with H$_2$/CO feed and then introduced to reactor at inlet at an amount of ethylene to give 2.5% and 6.2% ethylene in feed on Co and Ru catalysts, respectively. The total reactor pressure was then increased to the level necessary to maintain the H$_2$+CO partial pressure in the reactor at the level found before ethylene addition. The reactor was operated at these conditions for 4 to 24 hours. Ethylene/argon feed was then directed so that it entered the reactor, undiluted by H$_2$+CO, at a point in the reactor ⅓×L (L reactor length) down from inlet, while maintaining H$_2$+CO space velocity and partial pressure at its previous level. The reactor was operated at these conditions for 4 to 24 hours. The ethylene/argon feed was discontinued and reactor conditions returned to those of beginning in order to rule out irreversible deleterious effects of ethylene addition on synthesis activity and selectivity.

| Run | 119-342 | 119-339 |
|---|---|---|
| % Ethylene in Feed | 0 | 2.5 |
| Location Added Ethylene | None | Inlet |
| % Ethylene Converted | — | 99.5 |
| Selectivity (%) to | | |
| C$_2$H$_6$ | — | 86.5 |
| C$_3$+ | — | 13.5 |
| C$_3$+ Yield (%) | — | 13.5 |
| Selectivity (%)* | | |
| CH$_4$ | 9.4 | 8.3 |
| C$_2$ | 1.3 | — |
| C$_3$ | 2.7 | 3.3 |

| -continued | | |
|---|---|---|
| $C_4$ | 2.4 | 2.9 |
| $CO_2$ | 0.4 | 0.5 |
| $C_5^+$ | 83.8 | 92.9 |

*% of ethylene converted which appeared as these products.
**% of ethylene added which appeared as these products.
***Selectivity is defined as percent of the CO converted which appears as a given product (it is almost identical to weight percent). However, when ethylene is added some of the C-atoms come from it and the sum of selectivities is greater than 100%.
11.7% Co/0.5 Re/TiO$_2$, 200° C., 2,050 kPa, H$_2$ + CO, H$_2$/CO = 2.1/1 25–27% CO conversion.

The addition of ethylene ($C_2^=$) at reactor inlet lowers the CH$_4$ selectivity and increases $C_5^+$ selectivity. Most of the ethylene (at 2.5% concentration) is converted, but only 13.5% of the converted ethylene appears as desirable $C_3^+$ products; the rest (86.5%) is hydrogenated to ethane, which is unreactive towards further chain growth to $C_3^+$ at Fischer-Tropsch synthesis conditions and, thus, cannot be recycled without converting it to ethylene in a dehydrogenation reactor.

Example 4

Effect of Ethylene Feed-Ruthenium Catalysts

| Run | 121–455 | 121–454 |
|---|---|---|
| % Ethylene in Feed | 0 | 6.2 |
| Location Added Ethylene | None | Inlet |
| % Ethylene Converted Selectivity to (%)* | — | 97 |
| Ethane | — | 82 |
| $C_3^+$ | — | 18 |
| Yield (%) $C_3^{+**}$ | — | 17 |
| Selectivity (%)*** | | |
| CH$_4$ | 5.5 | 4.3 |
| $C_2$ | 0.7 | — |
| $C_3$ | 2.1 | 2.6 |
| $C_4$ | 3.5 | 4.0 |
| $CO_2$ | 0.7 | 0.7 |
| $C_5^+$ | 87.5 | 105.6 |

*% of ethylene converted which appeared as these products.
**% of ethylene added which appeared as these products.
***Selectivity is defined as percent of the CO converted which appears as a given product (it is almost identical to weight percent). However, when ethylene is added some of the C-atoms come from it and the sum of selectivities is greater than 100%.
1.2% Ru/TiO$_2$, 200° C., 1,700 kPa, H$_2$/CO = 2.1/1, 35–45% CO conversion.

Addition of ethylene to H$_2$/CO feed at reactor inlet (at 6.2% level) lowers the CH$_4$ selectivity from 5.5 to 4.3, while increasing the $C_5^+$ selectivity from 87.5 to 105.6%. Most of the ethylene added in (97%) is converted, of which only 18% appears as desirable $C_3^+$ products; the rest (82%) is hydrogenated to ethane, which is unreactive towards further chain growth to $C_3^+$ at Fischer-Tropsch synthesis conditions and, thus, cannot be recycled without converting it to ethylene in a dehydrogenation reactor.

Example 5

Top versus Below Inlet Feed Ethylene-Ru

There is a clear advantage to bypassing the reactor inlet by introducing the $C_2^=$ below the inlet at the same concentration. The CH$_4$ selectivity decreases further (from 4.3% to 3.9%), the $C_5^+$ selectivity increases (from 105.6% to 117.0%) and the activity of the catalyst is unaffected by the presence of ethylene, either at inlet or below the inlet of the reactor. The apparent reason for the improved product selectivity is an increase in the yield of $C_3^+$ from ethylene (the percentage of the ethylene feed converted to $C_3^+$) from 17% to 26% in spite of the lower ethylene conversion when added below the inlet. Below inlet addition dramatically decreases the hydrogenation selectivity (from 82% to 44%), while increasing the $C_3^+$ selectivity (from 18% to 56%). Therefore, it dramatically increases the efficiency of ethylene utilization while avoiding the formation of species such as ethane which cannot be polymerized further under Fischer-Tropsch conditions.

| Run | 121–453 | 121–454 |
|---|---|---|
| % Ethylene in Feed | 6.2 | 6.2 |
| Location Added | Below Top Third of Reactor | Top |
| Ethylene* | | |
| % Ethylene Converted Selectivity to (%) | 45.3 | 97 |
| Ethane | 44 | 82 |
| $C_3^+$ | 56 | 18 |
| Yield (%) $C_3^{+**}$ | 26 | 17 |
| Selectivity (%)*** | | |
| CH$_4$ | 3.9 | 4.3 |
| $C_2$ | — | — |
| $C_3$ | 3.4 | 2.6 |
| $C_4$ | 5.1 | 4.0 |
| $CO_2$ | 0.7 | 0.7 |
| $C_5^+$ | 117.0 | 105.6 |

*% of ethylene converted which appeared as these products.
**% of ethylene added which appeared as these products.
***Selectivity is defined as percent of the CO converted which appears as a given product (it is almost identical to weight percent). However, when ethylene is added some of the C-atoms come from it and the sum of selectivities is greater than 100%.
1.2% Ru/TiO$_2$, 200° C., 1,700 kPa, H$_2$/CO = 2.1/1, 35–45% CO conversion.

Example 6

Top versus Below Inlet Feed Ethylene-Co

There is a clear advantage to bypassing the rector inlet by introducing the $C_2^=$ below the inlet at the same concentration. The CH$_4$ selectivity decreases further (from 8.3% to 7.2%), the $C_5^+$ selectivity increases (from 92.9% to 99.3%) and the activity of the catalyst is unaffected by the presence of ethylene, either at inlet or below the inlet of the rector. The apparent reason is an increase in the yield of $C_3^+$ from ethylene (the percentage of the ethylene feed converted to $C_3^+$) (from 13.% to 27.3%), in spite of the lower ethylene conversion when added below the inlet. Below inlet addition dramatically decreases the hydrogenation selectivity (from 86.5% to 69.5%), while increasing the $C_3^+$ selectivity (from 13.5% to 30.5%). Therefore, it dramatically increases the efficiency of ethylene utilization, while avoiding the formation of species such as ethane which cannot be polymerized under Fischer-Tropsch conditions.

| Run | 119–336 | 119–339 |
|---|---|---|
| % Ethylene in Feed | 2.5 | 2.5 |
| Location Added | Below Top Third | Inlet |
| Ethylene | | |
| % Ethylene Converted Selectivity (%) to | 89.5 | 99.5 |
| $C_2H_6$ | 69.5 | 86.5 |
| $C_3^+$ | 30.5 | 13.5 |
| $C_3^+$ Yield (%) | 27.3 | 13.5 |
| Selectivity (%)* | | |
| CH$_4$ | 7.2 | 8.3 |
| $C_2$ | — | — |
| $C_3$ | 3.7 | 3.3 |
| $C_4$ | 3.7 | 2.9 |
| $CO_2$ | 0.4 | 0.5 |

| -continued | | |
|---|---|---|
| $C_5+$ | 99.3 | 92.9 |

*% of ethylene converted which appeared as these products.
**% of ethylene added which appeared as these products.
***Selectivity is defined as percent of the CO converted which appears as a given product (it is almost identical to weight percent). However, when ethylene is added some of the C-atoms come from it and the sum of selectivities is greater than 100%.
11.7% Co/0.5 Re/TiO$_2$, 200° C., 2,050 kPa, H$_2$ + CO, H$_2$/CO = 2.1/1
25-27% CO conversion.

What is claimed is:

1. A process for reducing methane formation and increasing liquid (C$_5$+) yields in a Fischer-Tropsch hydrocarbon synthesis process comprising adding an olefin to a gas feed and contacting said gas feed comprising a mixture of H$_2$ and CO with a catalyst at an elevated temperature of at least about 100° C., said addition of said olefin and said contacting with said gas feed occurring within the reactor bed in the area of the reactor bed below 10% of the distance from the top to the bottom of the reactor bed and above 10% of the distance from the bottom to the top of the reactor bed in an amount sufficient to reduce said methane formation, wherein said catalyst comprises a catalytic metal selected from the group consisting of iron, cobalt and ruthenium supported on an inorganic refractory oxide support.

2. The process of claim 1 wherein said olefin is obtained from the product stream of said process.

3. The process of claim 2 wherein said olefin is an alpha olefin of the type R—CH=CH$_2$ wherein R is hydrogen or an alkyl group having about 1 to about 17 carbon atoms.

4. The process of claim 2 wherein said olefin comprises a C$_2$-C$_{10}$ alpha olefin.

5. The process of either of claim 2 or 3 wherein the amount of olefin present, on an olefin to CO mole ratio, ranges from about 1/100 to 5/1.

6. The process of claim 5 wherein said temperature ranges from about 100° C. to 500° C.

7. The process of claim 1 wherein said catalyst comprises ruthenium, cobalt or iron supported on titanium dioxide.

8. The process of claim 7 wherein the mole ratio of H$_2$ to CO of the feed ranges from about 0.5 to about 10.

* * * * *